United States Patent
Corbett et al.

(10) Patent No.: US 9,829,525 B2
(45) Date of Patent: Nov. 28, 2017

(54) SURFACE CHARGE MEASUREMENT

(75) Inventors: Jason Corbett, Malvern (GB); Fraser McNeil-Watson, Malvern (GB); Robert Jack, Malvern (GB)

(73) Assignee: Malvern Instruments Limited, Malvern (GB)

( * ) Notice: Subject to any disclaimer, the term of this patent is extended or adjusted under 35 U.S.C. 154(b) by 660 days.

(21) Appl. No.: 14/126,673

(22) PCT Filed: Jun. 13, 2012

(86) PCT No.: PCT/GB2012/051336
§ 371 (c)(1),
(2), (4) Date: Sep. 29, 2014

(87) PCT Pub. No.: WO2012/172330
PCT Pub. Date: Dec. 20, 2012

(65) Prior Publication Data
US 2015/0022212 A1    Jan. 22, 2015

Related U.S. Application Data

(60) Provisional application No. 61/497,385, filed on Jun. 15, 2011.

(51) Int. Cl.
*G01N 27/416*    (2006.01)
*G01N 27/42*    (2006.01)
(Continued)

(52) U.S. Cl.
CPC .............. *G01R 29/24* (2013.01); *G01N 21/51* (2013.01); *G01N 2021/513* (2013.01)

(58) Field of Classification Search
CPC ..................................................... G01R 29/24
(Continued)

(56) References Cited

U.S. PATENT DOCUMENTS

2004/0251134 A1   12/2004  Sekiwa et al.
2006/0114467 A1*   6/2006  Nicoli .............. G01N 27/44721
                                                        356/450

(Continued)

FOREIGN PATENT DOCUMENTS

CN    1517704    8/2004
EP    0990888    4/2000
(Continued)

OTHER PUBLICATIONS

Office Action (Chinese Patent Application Serial No. 2012800276951), mailed Nov. 19, 2014 (with translation).
(Continued)

*Primary Examiner* — Edward Tso
*Assistant Examiner* — Ahmed Omar
(74) *Attorney, Agent, or Firm* — Kristofer E. Elbing

(57) ABSTRACT

The invention relates to methods and apparatus for determining properties of a surface. Embodiments disclosed include an apparatus for measuring a surface charge of a sample, comprising: a sample holder having an opposed pair of electrodes and configured to hold a sample in position in a measurement volume between the electrodes such that a planar surface of the sample is aligned orthogonal to the electrode surfaces; a measurement chamber for containing a measurement liquid and having an open end configured to receive the sample holder to position the electrodes in a preset orientation; a laser light source positioned and configured to direct a laser beam through the measurement chamber between the electrodes and parallel to the planar surface of the sample when the sample holder is received in the measurement chamber; and a detector positioned and configured to detect scattered light from the measurement volume, wherein the apparatus is configured to allow for (Continued)

detection of the scattered light by the detector over a range of distances from the surface of the sample.

9 Claims, 15 Drawing Sheets

(51) Int. Cl.
  *G01R 29/24* (2006.01)
  *G01N 21/51* (2006.01)
(58) Field of Classification Search
  USPC .......................................................... 324/425
  See application file for complete search history.

(56) References Cited

U.S. PATENT DOCUMENTS

| | | | | |
|---|---|---|---|---|
| 2008/0208511 | A1* | 8/2008 | Trainer | G01N 15/0205 702/128 |
| 2012/0048737 | A1* | 3/2012 | Yamaguchi | G01N 21/51 204/645 |

FOREIGN PATENT DOCUMENTS

| | | | | |
|---|---|---|---|---|
| EP | 1154266 | | 11/2001 | |
| EP | 1154266 | | 9/2002 | |
| EP | 1464956 | | 6/2004 | |
| GB | 2317706 | | 11/1997 | |
| JP | 10104188 | | 4/1998 | |
| JP | 2001264282 | | 9/2001 | |
| JP | 2002005888 | | 9/2002 | |
| JP | 2003028779 | | 7/2003 | |
| JP | 2010078468 | | 4/2010 | |
| JP | 2010-101705 A | * | 5/2010 | ............ G01N 27/26 |
| JP | 2010101705 | | 5/2010 | |
| JP | 2010101705 | | 6/2010 | |
| WO | 2010041082 | | 4/2010 | |

OTHER PUBLICATIONS

Office Action (Japanese Patent Application Serial No. 2014530309), mailed May 31, 2016 (w translation).

Decision to Grant a Patent (Japanese Patent Application Serial No. 2014530309), dated Sep. 20, 2016 (w translation).

Communication about intention to grant a European patent (European Patent Application Serial No. 12740387), May 1, 2017.

Text intended for grant (European Patent Application Serial No. 12740387), May 1, 2017.

Notification to Grant Patent Right for Invention(PCT) (Translated) (Chinese Patent Application Serial No. 201280027695), Mar. 3, 2016.

Notification to Grant Patent Right for Invention(PCT) (Original) (Chinese Patent Application Serial No. 201280027695), Mar. 3, 2016.

Argument (Translated), (Chinese Patent Application Serial No. 201280027695), Dec. 14, 2015.

* cited by examiner

SURFACE CHARGE MEASUREMENT

CROSS-REFERENCE TO RELATED APPLICATIONS

This application is a national phase application of PCT application number PCT/GB2012/051336, filed Jun. 13, 2012, which claims priority to US provisional application number 61/497,385, filed Jun. 15, 2011. Both of these applications are herein incorporated by reference.

FIELD OF THE INVENTION

The invention relates to methods and apparatus for determining properties of a surface. Exemplary embodiments include methods and apparatus for determining a surface zeta potential by electro-osmotic flow measurement in a dip cell arrangement.

BACKGROUND OF THE INVENTION

The well known phenomenon of streaming potential is typically used to measure surface potential or charge of a material in an electrolyte. Measurements of capillary flow and on dispersions of finely divided particles may be used to determine surface charge. Measurement techniques generally employ a specialist instrument dedicated solely to such measurements. Measurements using capillary flow or dispersed particles may require that the sample material be in a particular format that may not always be convenient or straightforward to prepare.

U.S. Pat. No. 7,217,350 discloses a method of automatically determining an electric charge-related characteristic or derived parameter of particles in a dispersion or of a cell wall, in which a dispersion is illuminated with light from a light source and light scattered by particles in a detection volume is detected. In one arrangement the detection volume comprises a transparent capillary cell with a pair of electrodes at opposing ends, forming a closed volume for a dispersion of particles in a liquid. In another arrangement a pair of electrodes is provided on opposing side walls of a cuvette that is partly filled with a liquid sample.

U.S. Pat. No. 7,449,097 discloses an electrophoretic mobility measuring apparatus comprising a cell for confining a sample, the cell having a transparent electrode side wall and another electrode on an opposing cell wall. A voltage is applied across the electrodes and light is incident upon the inside of the cell through the transparent electrode. Scattered light is received through the transparent electrode and a Doppler displacement is measured.

US 2011/0210002 discloses a method and apparatus for measurement of electrophoretic mobility of particles and molecules in solution, in which a sample of particles is placed in a cell containing two electrodes across which is applied an alternating electric field. A monochromatic light beam passes through the sample and light scattered by particles is collected and collimated as it exits the cell. Optical phase information is used to measure particle movement.

EP 2423671 discloses a particle characterization cell and instrument, in which a tubular cell main body forms an internal space with a pair of electrodes arranged to face each other in the internal space, laser light irradiating a liquid sample in the internal space being scattered by particles in the liquid sample and detected by a light detecting part.

Each of the above mentioned documents disclose measurement of electrophoretic mobility of samples in the form of finely divided particles suspended in an electrolyte liquid.

SUMMARY OF THE INVENTION

Several aspects of the invention are presented in this application. Systems according to at least some of the aspects of the invention can be advantageous in that they can provide a convenient, accurate; and reliable way to measure sample surface potentials.

In accordance with a first aspect there is provided an apparatus for measuring a surface charge of a sample, comprising:
 a sample holder having an opposed pair of electrodes and configured to hold a sample in position in a measurement volume between the electrodes such that a planar surface of the sample is aligned orthogonally to the electrode surfaces;
 a measurement chamber for containing a liquid electrolyte and having an open end configured to receive the sample holder to position the electrodes in a preset orientation;
 a laser light source positioned and configured to direct a light beam through the measurement chamber between the electrodes and parallel to the planar surface of the sample when the sample holder is received in the measurement chamber; and
 a detector positioned and configured to detect scattered light from the measurement volume,
 wherein the apparatus is configured to allow for detection of the scattered light by the detector over a range of distances from the surface of the sample.

Detection of scattered light over a range of distances from the surface of the sample may be achieved by having a large illuminated area with multiple detection points, having multiple illumination sources and multiple detection points, and/or by allowing relative movement of the light beam and sample holder. The first option may be achieved by the light beam having a width extending over the range of distances, or multiple light beams, and a detector, or multiple detectors, positioned for measuring scattered light at multiple detection points at defined distances from the sample surface. The second option, which may be provided in addition to the first, may be achieved by allowing manual or automatic movement of the sample in situ relative to the light beam and/or by moving the light beam relative to the sample surface.

An advantage of the apparatus according to the invention is that surface charge measurements can be taken of a material in a quicker and more convenient way compared to existing surface charge measurement systems, for example those using capillary cells. In particular, the relative orientation of the sample surface to the electrodes, and the arrangement where the sample holder is insertable in, and removable from, a measurement chamber, allows for a convenient measurement system for easily prepared sample geometries.

The sample holder may comprise a first portion and a second portion, where the electrode pair is disposed at a distal end of the second portion, the sample holder comprising an actuation mechanism for translating the second portion relative to the first portion. An advantage of the actuation mechanism is that the sample can be positioned such that the sample surface is in a predefined position relative to the laser light beam, so that accurate and repeatable measurements can be taken as the sample is translated relative to the light beam.

The actuation mechanism may be configured to translate the second portion relative to the first portion in a direction parallel to the electrode surfaces, or orthogonal to the surface of the sample. Maintaining an orthogonal arrangement between the light beam and the electrodes, and between the electrodes and the sample surface, ensures that the light beam can be used to accurately measure the charge properties of the surface when immersed in the electrolyte.

The actuation mechanism may comprise a rotatable element such as a calibrated micrometric screw for linear translation of the second portion relative to the first portion, an advantage of which is in repeatable positioning over a range of positions of the sample relative to the laser light beam. The actuation mechanism may be manually operable, or may be electrically actuated.

The sample holder may be configured to be located in the measurement chamber in two or more distinct orientations such that the electrodes are located in two or more respectively different positions relative to the measurement chamber. The sample holder may for example be configured such that the electrodes are rotated 180 degrees between the first and second distinct orientations. An advantage is that the two or more configurations can be used to position the sample in preset positions relative to the laser light beam for simple and quick measurements on the sample without the need for fine adjustment of the sample holder. The number of distinct configurations is preferably only two, although further configurations are possible. The sample holder and measurement chamber may comprise correspondingly shaped stepped mating surfaces to achieve the two or more configurations when the stepped mating surfaces are engaged with each other.

The apparatus may further comprise a calibration jig configured to hold the sample holder in a predefined position such that the sample surface in position between the electrodes can be translated to a predetermined location relative to the first portion of the sample holder, and thereby relative to the laser beam when the sample holder is positioned in the measurement chamber. An advantage of using a calibration jig is that the sample can be accurately positioned without the need to determine the distance between the laser light beam and the sample surface when the sample holder, is positioned in the measurement chamber.

The apparatus is preferably configured to determine a measure of movement of tracer particles suspended in the electrolyte in the measurement volume between the electrodes from scattered light detected by the detector. The measurement of particle movement may be determined by Doppler analysis of the scattered light. The apparatus may be further configured to determine a measure of surface potential of the sample by extrapolation of two or more measurements of movement of tracer particles at different relative distances between the laser light beam and the sample surface.

The apparatus is preferably configured to apply an alternating voltage to the opposed pair of electrodes to provide an alternating electric field between the electrodes across the planar surface of the sample during detection of the scattered light by the detector. The alternating voltage may be in the form of a square wave comprising half cycles with an optional interval between each half cycle where no voltage is applied. Each half cycle, i.e. the portion of the alternating voltage where either a positive or a negative voltage is applied across the electrodes, may be of 75 ms or longer in duration, optionally between 75 ms and 1200 ms, and further optionally around or below 300 ms. The optional interval between each half cycle may be between 0 and 1000 ms, with a particular preferred interval of around 200 ms.

In accordance with a second aspect there is provided a method of measuring surface charge of a sample, comprising:

providing a sample holder having an opposed pair of electrodes with a sample held in position in a measurement volume between the electrodes such that a planar surface of the sample is aligned orthogonal to the electrode surfaces;

receiving the sample holder in an open end of a measurement chamber containing a liquid electrolyte to position the electrodes in a preset orientation;

directing a light beam from a laser light source through the measurement chamber between the electrodes and parallel to the planar surface of the sample with the sample holder received in the measurement chamber; and detecting scattered light from tracer particles suspended in the liquid electrolyte in the measurement volume with a detector wherein scattered light is detected by the detector over a range of distances between the laser beam and the planar surface of the sample.

Optional and preferable features of the second aspect of the invention may correspond with those of the first aspect, as described above.

In accordance with a further aspect of the invention there is provided a zeta potential measurement apparatus for measuring a zeta potential of a surface of a sample using tracer particles, comprising:

a first electrode surface, a second electrode surface separated from the first electrode surface along a first axis, a vessel defining a measurement volume between the first and second electrodes, and a holder for holding the sample adjacent the measurement volume at a position between the first and second electrodes, and an optical detector responsive to one or more locations within the measurement volume and operative to detect motion of the tracer particles at the plurality of different locations within the measurement volume.

The apparatus may further include a motive mechanism provided between the sample and the detector to induce relative motion between the sample and detector to cause the detector to be responsive to a plurality of the locations. The motive mechanism may be manually actuated. The motive mechanism may be joggle-based, i.e. based on the sample holder being locatable in the measurement chamber or vessel in two or more distinct orientations. The motive mechanism may be electrically actuated. The detector may be an autocorellating PALS detector.

The apparatus may further include a processor operative to calculate the zeta potential based on differences in reported potential and displacement at the plurality of different locations.

The electrode surfaces may be parallel and the plurality of locations may be positioned along a second axis perpendicular to first axis.

The first and second electrodes, the vessels, and the holder may all be held in a removable cuvette that is constructed to sit in an instrument that includes the detector.

In accordance with a further aspect of the invention there is provided a method of obtaining zeta potential measurements for a surface of a sample using tracer particles, comprising:
  contacting the sample with an electrolyte,
  introducing tracer particles in the electrolyte,
  applying an electric field across the electrolyte, and
  measuring displacement of the tracer particles at one or more positions within the electrolyte.

The method may further include the step of deriving the zeta potential from results of the step of measuring.

The method may be applied to a sample that includes a plastic material. The method may be applied to a sample that includes a solid biological material.

The step of measuring displacement may include measuring a displacement at at least two positions, optionally at least three positions, within the electrolyte.

In accordance with a further aspect of the invention there is provided a method of obtaining zeta potential measurements for a surface of a sample using tracer particles, comprising:
  means for contacting the sample with an electrolyte with suspended tracer particles,
  means for applying an electric field across the electrolyte, and
  means for measuring displacement of the tracer particles at one or more positions within the electrolyte.

The means for contacting may include a dip cell that includes means for holding the electrolyte with suspended tracer particles and means for holding the sample at a predetermined position in the means for holding.

DETAILED DESCRIPTION

Aspects and embodiments of the invention are described in further detail below by way of example and with reference to the enclosed drawings in which.

Figure 1:
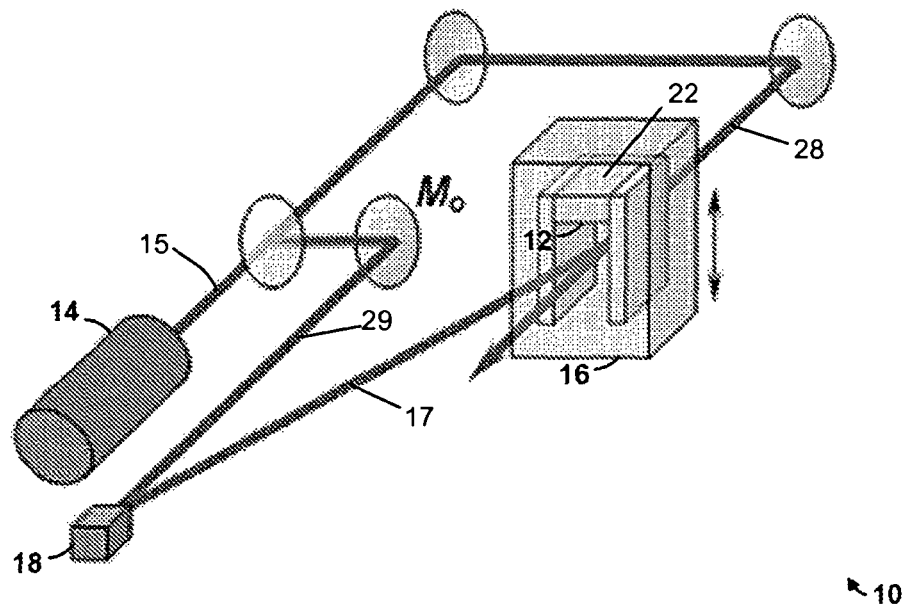
FIG. 1 is a perspective schematic diagram of an illustrative zeta potential measurement instrument according to the invention.

Referring to FIG. 1, an exemplary surface charge measurement instrument 10 according to an aspect of the invention includes a light source 14, a sample cell 16 for holding a sample 22 under test with its test surface 12 in contact with an electrolyte, and a detector 18. The instrument 10 may be used to determine the zeta potential of the test surface 12 of the sample 22 under test. Although other configurations are possible, the light source 14 and the detector 18 preferably form part of a particle measurement system along with other optical elements that enable the system to perform a laser Doppler phase electrophoretic analysis light scattering measurement protocol, such as is described in reference [12]. Particle measurement instruments of this type are available from Malvern instruments Ltd of Malvern, UK, examples of which are described further in international patent application PCT/GB2009/051350, published as WO/2010/041082 and as U.S. Pat. No. 9,341,564, issued May 17, 2016, which is herein incorporated by reference.

Figure 2:
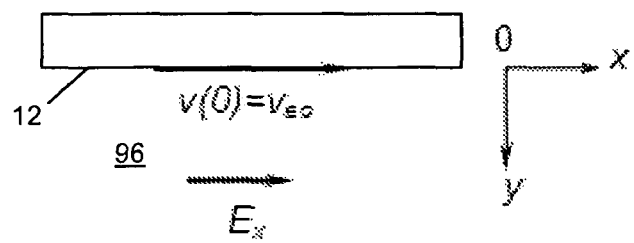
FIG. 2 is a schematic diagram illustrating flow geometry for a surface under test.

Referring also to FIG. 2, the instrument 10 operates according to an optical technique that measures the electroosmotic flow of an electrolyte near a single charged test surface 12 with an external field applied parallel to the surface. The technique uses a single test plate presented to the optical detection system in a convenient 'dip cell' format that can fit inside a standard type of cuvette and can therefore be used in instrumentation intended for electrophoresis measurements, such as the Zetasizer range of instruments from Malvern Instruments Ltd.

A surface 12 under test is immersed in an electrolyte 96 with an external electric field $E_x$ applied. The technique is characterized by displacements of the order of 100's of micrometres (μm) and the slipping plane of the surface 12 under test can then be assumed to coincide with the plane of y=0. The electric field $E_x$ and the presence of the ionic species within the electrolyte cause electro-osmotic fluid motion along the surface at y=0.

Assuming that the system has no pressure gradients, is slow flowing and in a steady state, the Navier-Stokes equation reduces to $$\rho v = \eta \left[ \frac{d^2 v}{dx^2} + \frac{d^2 v}{dy^2} \right] \quad (1)$$

where v(t,x,y) is the component of fluid velocity parallel to the boundary, ρ is the fluid density and η is the fluid viscosity. The co-ordinate x is parallel to the boundary, and y is perpendicular. Because there is no flow perpendicular to the boundary, continuity implies that v is not a function of x, and the equation simplifies to the following one dimensional homogenous heat or diffusion equation:

$$v = k \left[ \frac{d^2 v}{dy^2} \right] \quad (2)$$

where k=η/ρ. This, with the initial condition that v(0,y)=0 and boundary condition v(t,0)=$v_{eo}$ where $v_{eo}$ is the fluid velocity at the boundary we have a problem on the half line (0, ∞) with homogenous initial conditions and Dirichlet boundary conditions and has a Green function solution that can be expressed in closed form as follows:

$$v(y, t) = \int_0^\infty \frac{1}{\sqrt{4\pi k(t-s)^3}} \exp\frac{y^2}{4k(t-s)} v_{eo} ds \quad (3)$$

This has the following closed form solution:

$$v(y, t) = v_{eo} \left[ 1 - erf\left( \frac{y}{2\sqrt{kt}} \right) \right] \quad (4)$$

where erf is the error function. For water at 25° C. the term in square brackets in equation (4) disappears at y≥750 μm for t≥75 ms or y≥1.5 mm for t≥300 ms. Time intervals of this magnitude are typical for monitoring electrophoretic motion using PALS and adjustment of the surface under test with respect to the detection optics is easily achieved within these distances with a micrometer stage. Therefore, a fit of equation (4) to measurements of $v_i(y_i)$ at various points $y_i$ can then be extrapolated to the y-axis intercept to yield $v_{eo}$. This is described in more detail in section 2.2.2.1 of reference [35]. The relationship between the surface zeta potential ζ and $v_{eo}$ is given by:

$$\frac{v_{eo}}{E_x} = \frac{\varepsilon \zeta}{\eta} \quad (5)$$

where $E_x$ is the electric field strength, ε the electrolyte relative permittivity and η the electrolyte viscosity (see also reference [11]).

The fluid motion measurement (at points $y_i$) is achieved by detection of the movement of tracer particles dispersed in the electrolyte alongside the surface under test, with the mobility being measured using a PALS (Phase Analysis Light Scattering) technique.

Figure 3:
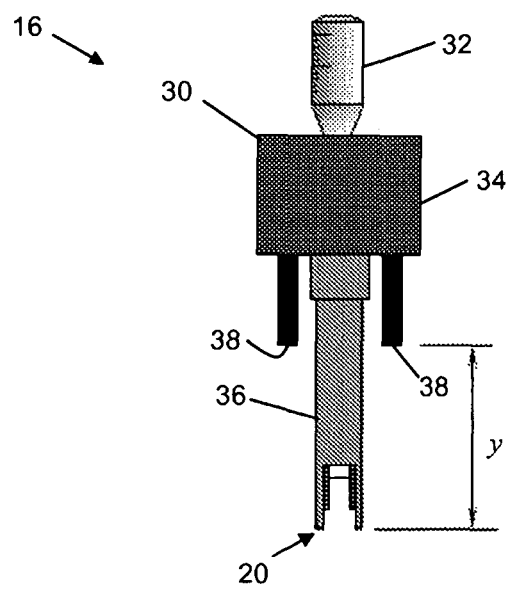
FIG. 3 is an elevation view diagram of a sample holder test cell for the instrument of FIG. 2.
Figure 4:
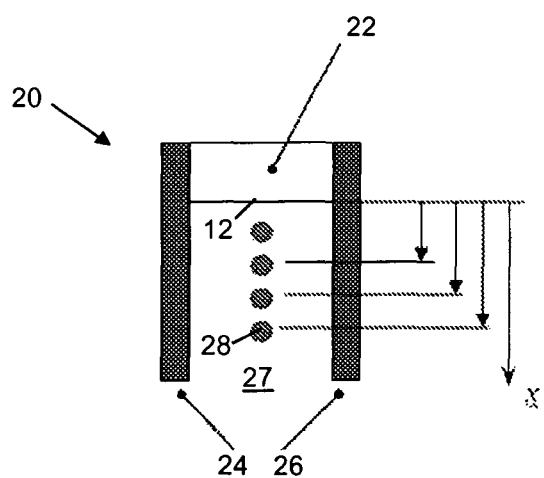
FIG. 4 is a cross-sectional diagram of a sample holder test cell head for the instrument of FIG. 2 showing different measurement beam positions for different test cell head positions.
Figure 5:
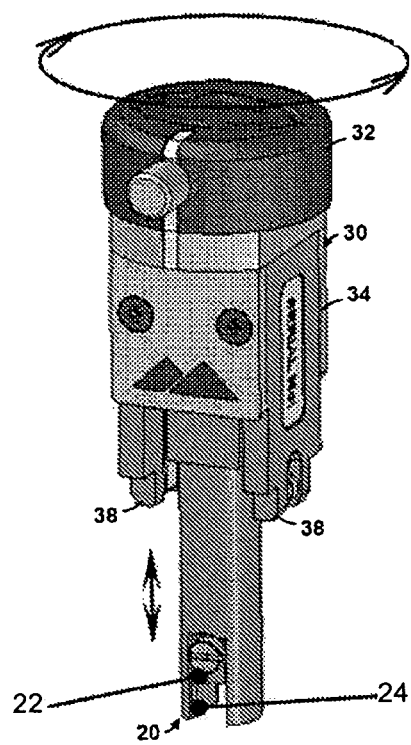
FIG. 5 is a perspective drawing of an implementation of the sample holder test cell of FIG. 3.

Referring also to FIGS. 3 to 5, the sample holder test cell 16 includes a first portion 34 and a second portion in the form moveable section 36 having a test cell head 20 supported by, and located at a distal end. The test cell head 20, further detailed in FIG. 4, includes a pair of electrodes 24, 26, which are preferably plate-shaped, i.e. planar. The electrodes 24, 26 are positioned either side of a measurement volume 27 in which a test sample 22 can be located with a planar test surface 12 oriented orthogonally to the planar surfaces of the electrodes 24, 26. In use, the test cell head 20 comprising the electrodes 24, 26 and test sample 22 is immersed in an electrolyte that includes tracer particles, the electrolyte providing a medium across which an electric field is applied by the electrodes 24, 26.

The sample holder 30 includes an adjustment mechanism 32, such as a micrometer, which is supported by a static section 34. The adjustment mechanism 32 allows the position of the test cell head 20 to be adjusted relative to the static section 34 in a direction normal to the test surface 12 so that a measurement beam 28 (FIG. 4) from the light source 14 is directed across the test surface 12 over a range of distances from the test surface 12. The supporting section 32 of the test cell body 30 may include one or more interface surfaces 38 that interface mechanically and electrically with portions of the instrument to allow the test cell to be removably and precisely positioned in the instrument with respect to the measurement beam 28. In the exemplary embodiment illustrated in FIG. 5, the test cell 16 is designed to conform to a standard form factor for test cuvettes for the above mentioned Zetasizer instrument line. The adjustment mechanism 32 may be manually operated or may be motorized.

Figure 6:
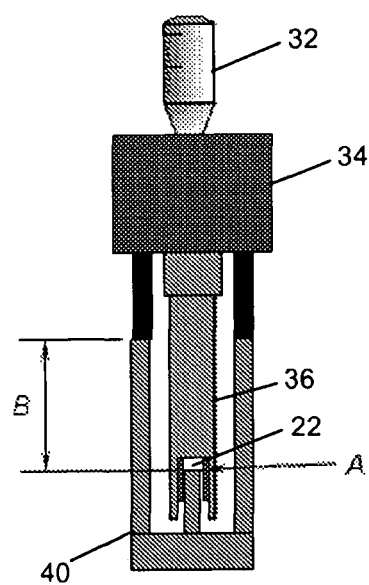
FIG. 6 is a plan view diagram of the sample holder test cell of FIG. 3 in position in an adjustment or calibration jig.

The test cell 16 may be mounted in a calibration jig 40, as shown in FIG. 6. The adjustment mechanism 32 can then be used to adjust the position of the surface of the test sample 22 until there is no gap between the surface and a corresponding mating surface of the calibration jig 40 (indicated at position A in FIG. 6). A user can then set the adjustment mechanism 32, for example in the form of a micrometer, to a required measurement position from this datum. This technique allows for different test plate thicknesses to be accommodated. The test cell 16 can then be removed from the jig and immersed in the measurement chamber, or cuvette, containing tracer particles dispersed in the target liquid electrolyte, and placed in the instrument for measurement.

Figure 7:
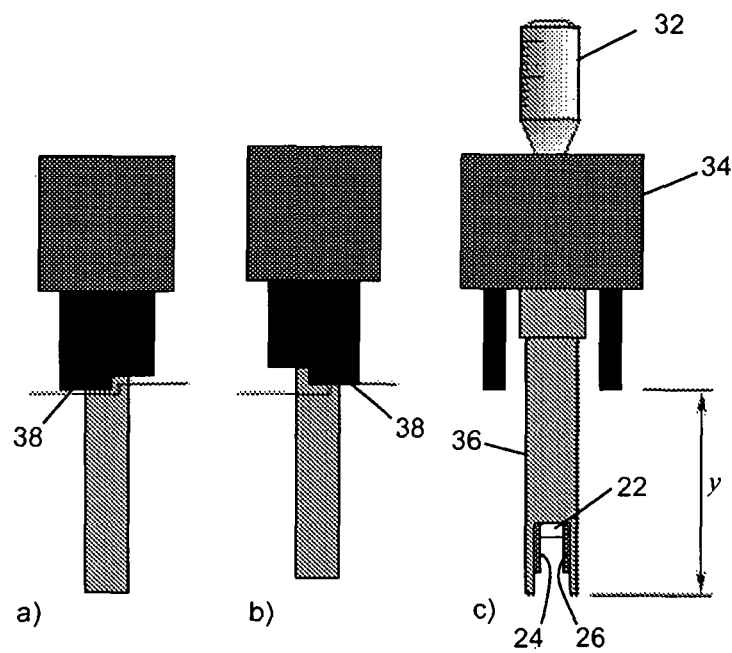
FIGS. 7a to 7c are side elevation views of an exemplary sample holder test cell configured for two distinct orientations relative to a measurement chamber.

In general, the data obtained using the test cell of the type described herein tend to be highly reproducible, with standard engineering tolerances being sufficient to reduce uncertainties to a minimum. For increased reproducibility, an additional feature may be incorporated in the test cell, an example of which is illustrated in FIG. 7. In this embodiment, a micrometer adjustment mechanism is used to set the correct height of the test surface with respect to the beam to accommodate the thickness of the test sample, for example using a calibration jig as described above. Once calibrated, the test cell may be positioned in two or more preset measurement positions relative to the measurement chamber, each position having a preset distance between the measurement beam and the test surface of the sample. This may be achieved by providing a stepped region 38 on the static or supporting section 34 of the test cell, the stepped region 38 allowing for two different positions depending on the orientation of the test cell relative to the measurement chamber. In the exemplary embodiment illustrated in FIG. 7, the test cell may be rotated through 180° ($\pi$ radians) to select which relative position is chosen. If the linear assumption according to the relationship in equation 2 is correct, two measurement positions should be sufficient to obtain a value for both m and $v_{eo}$. For increased accuracy, however, further preset positions may be preferred, which may be achieved for example by providing a series of two or more stepped regions allowing for a corresponding plurality of different measurement positions.

In one exemplary embodiment, the test cell may have a 500 μm pitch thread and the cell position y, i.e. the distance between the static section 34 and the end of the moveable portion 36, may be adjusted by winding an adjustment knob against a biasing force provided by a spring, thereby reducing hysteresis and relative positional uncertainty to low or negligible levels. In order to set a zero point for a plate of arbitrary thickness, the cell can be adjusted downwards relative to the measurement chamber until the laser beam is on the point of being obscured, as determined by monitoring a count rate in the forward angle. In this exemplary embodiment, the laser beam passes through the cell as shown in FIG. 1 with a beam width or around 40 μm, resulting in a maximum uncertainty of around ±20 μm. Particle mobility data may also be recorded and the results can be reduced using the relationship of equation 4.

Figure 9:
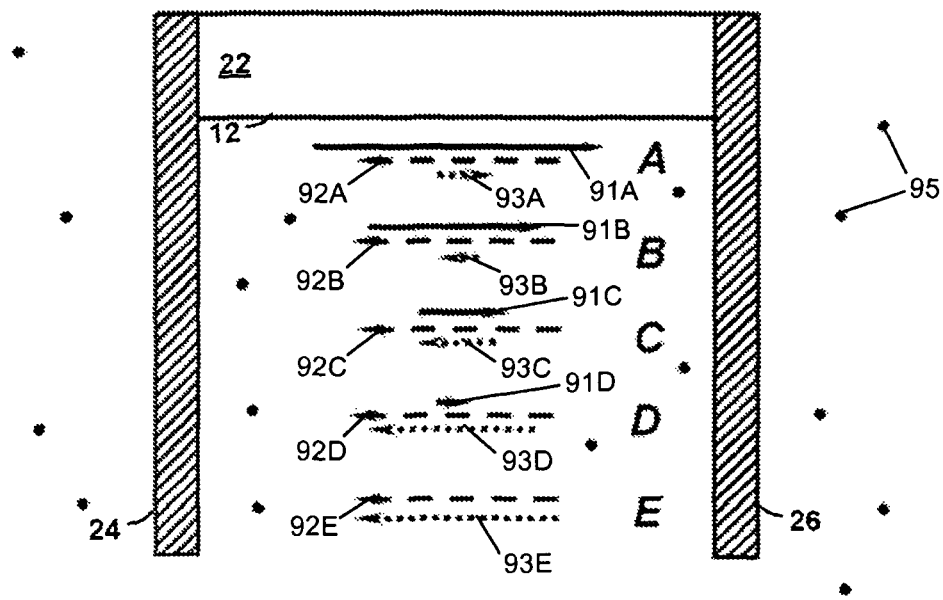
FIG. 9 is a schematic diagram of the test cell electrode assembly of FIG. 4 illustrating particle and fluid flow resulting from voltage applied to the cell at different measurement positions.

In operation, referring also to FIG. 9, charged tracer particles 95 suspended in the liquid electrolyte 96 move under the application of the electric field between the opposing electrodes 24, 26. The tracer particles 95 scatter light from the illuminating beam, which is detected by the detector 18. By use of a reference beam 29 (FIG. 1) split off from the incident beam 15 prior to illuminating the sample, the phase of the scattered light 17 relative to the incident light 15 can be measured. This phase is linearly related to the speed of the tracer particles 95 in the measurement liquid 96. Since the static or supporting section 34 of the test cell 30 is fixed relative to the illuminating optical measurement beam 28 (FIG. 4), the plate position can be altered by means of the adjustment mechanism 32 (FIG. 5), such as a micrometer, thereby translating the moveable section 36 (FIG. 3) relative to the supporting section 34 and therefore with respect to the measurement beam 28. Multiple measurements can thereby be taken for a sample with the measurement beam 28 at multiple distances from the test sample surface 12.

As illustrated schematically in FIG. 9, on the application of an electric field across the measurement volume between the electrodes 24, 26, the tracer particles 95 move under the influence of both the electro-osmotic motion of the fluid, $v_i(y_i)$ (indicated by solid vectors 91A-D) and due to electrophoretic motion, $v_{ep}$ (indicated by dashed vectors 92A-E). The total detected motion is given by the sum of these vectors, which in FIG. 9 is indicated by dotted vectors 93A-E. The field strength, $E_x$, can be determined from a measurement of the conductivity of the measurement liquid and a measurement of electric current during application of the field. This tends to yield a more accurate estimate of $E_x$ than by calculating the field from the potential applied to the cell.

Figure 8A:
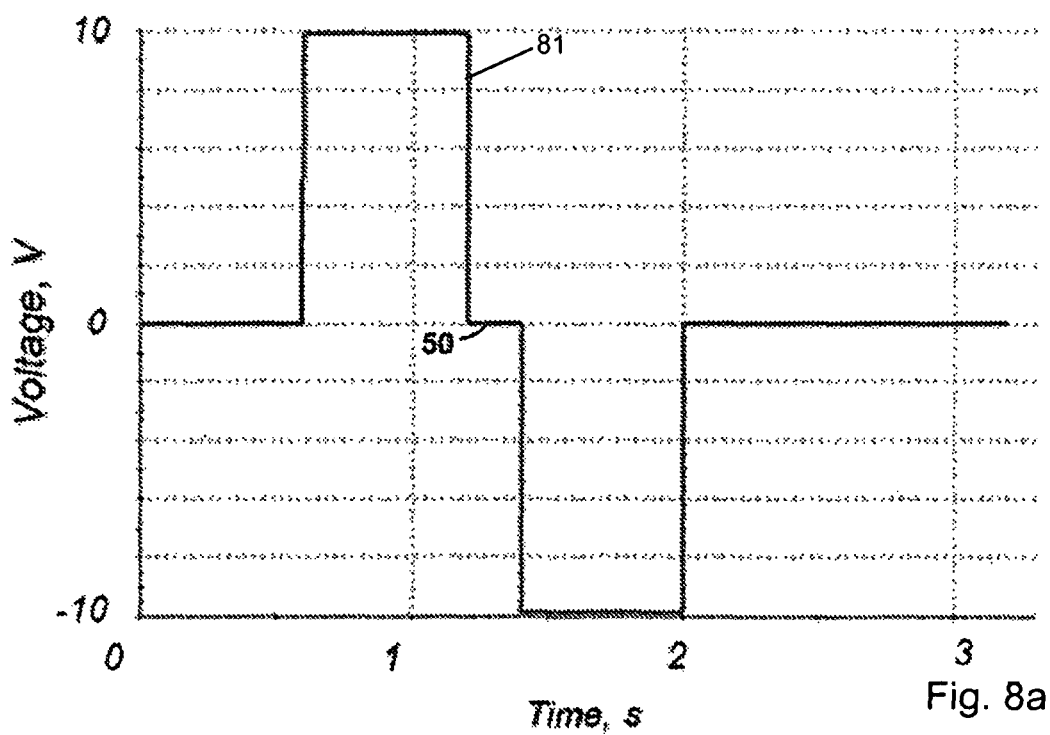
FIG. 8a is a plot of voltage applied to the test cell of FIG. 3 as a function of time.

FIG. 8a illustrates a plot of voltage applied to the electrodes of an exemplary test cell over time. In this case, the voltage is switched at a frequency of around 0.42 Hz, which is done to minimize any polarization concentration effects due to charge migration, which can cause increased uncertainty in the current estimate during the field application. An off-time 50 of around 200 ms between successive applications of opposing voltages over 600 ms periods is used in order to allow the system to relax to zero before a subsequent reverse polarity is started.

Figure 8B:
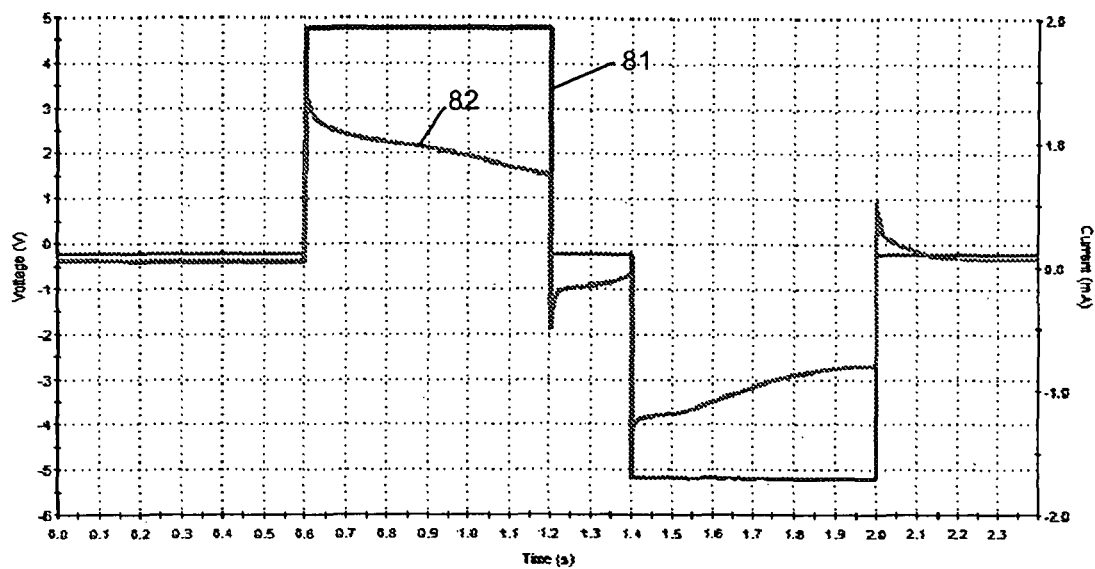
FIG. 8b is a plot of voltage applied to the test cell along with current passing through the test cell as a function of time.

FIG. 8b is a further plot of voltage 81 (left hand scale) and current 82 (right hand scale) as a function of time for an exemplary test cell. The voltage 81 is applied in the form of a series of square wave pulses, and the resulting current 82 peaks after the rising and falling edges of each pulse, followed by a gradual decay.

Figure 10A:
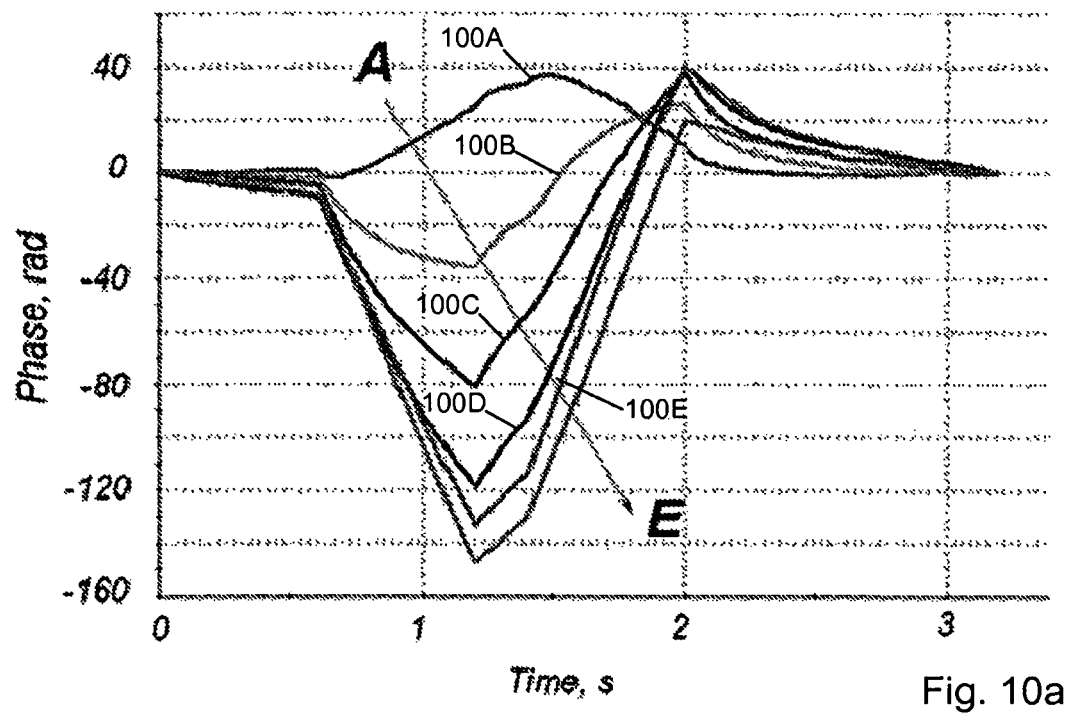
FIG. 10a is a family of plots of displacement (as indicated by phase) as a function of time for the measurement positions A to E illustrated in FIG. 9.
Figure 10B:
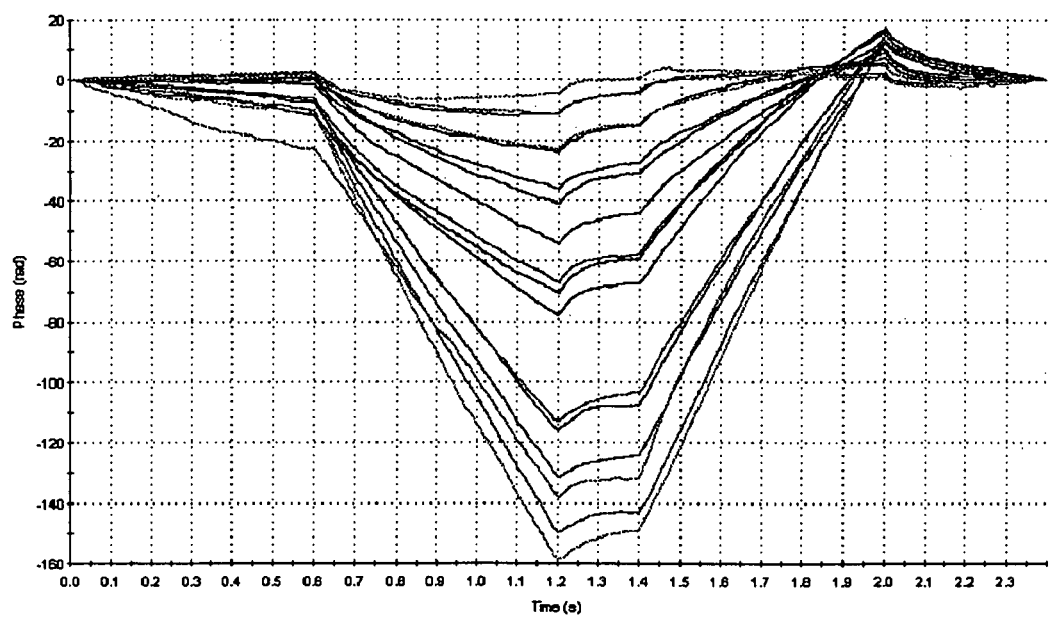
FIG. 10b is a further family of plots of displacement as a function of time for an increased number of measurement positions.

FIG. 10a illustrates a series of plots of phase (corresponding to particle displacement) as a function of time. The displacement per unit time (i.e. particle velocity) falls to around zero during the interval between successive voltage pulses. The overall displacement during each on-time pulse is taken as the average over the whole of the on-time period. This is based on a simplified model that ignores effects such as those due to inertia or pressure gradients but, as the results in the following sections show, this simple model provides measurements that are reasonably linear, in accordance with the relationship in equation 2, and which yield results that are precise and accurate in comparison to literature values based on other techniques. FIG. 10b illustrates a similar series of plots of phase as a function of time, for an increased number of beam positions relative to the sample surface.

Different measurement strategies can be employed to obtain a measure of surface charge of a sample. A set of measurements may be taken using a slowly varying field, as described above, at multiple beam positions, the positions set using adjustment of a micrometer. The micrometer may be motorised or manually adjusted. Slowly reversing field measurements may alternatively be taken at two positions only, for example by reversing the orientation of a suitably configured sample holder, as illustrated in FIG. 7 and described above. This may lead to increased uncertainty due to an extrapolation based only on two data points, but has an advantage of simplifying operation and improving repeatability.

Alternative types of measurements can be performed where one or two positions are used for the measurement. An appropriate model is fitted to the slow field phase plot and the electro-osmosis and electrophoresis calculated from the model. The electrophoresis may be measured either at the same position as the slow field or at the second positions, further away from the wall. This measurement strategy allows the determination of the sign of the wall charge, and is discussed in more detail in U.S. Pat. No. 7,217,350 and EP 1154266, which are both herein incorporated by reference.

Figure 11:
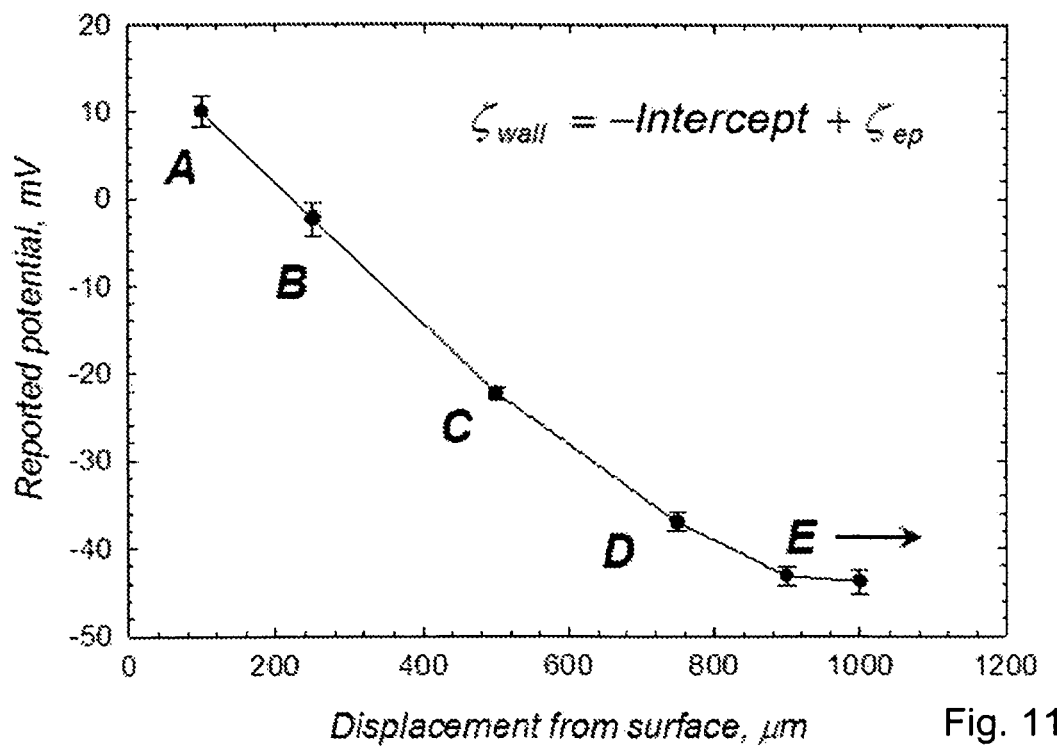
FIG. 11 is a plot of reported potential as a function of displacement from the sample surface for the measurement positions illustrated in FIG. 9.

The reported zeta potential values from measurements taken on a sample consisting of a PTFE block immersed in a pH 9.2 buffer and using Carboxylated latex tracer particles are shown in FIG. 11, as plotted against the displacement from the surface. As the optical detection position moves away from the surface (points A to D), the electro-osmotic contribution to the resulting motion reduces in value until, at some position E, the detected motion is in effect only the electrophoretic motion of the tracer from which the tracer zeta potential $\zeta_{ep}$ can be calculated (corresponding to the region between positions D and E in FIG. 11). The y-axis intercept can be extrapolated from a linear fit to the data over points A to D and the surface zeta potential at the slipping plane, i.e. where y=0, is then given by the following:

$$\zeta_{wall} = -\text{Intercept} + \zeta_{ep} \quad (6)$$

The data were reduced using a least squares linear regression of the potentials reported at each displacement against the displacement from the surface. The standard error in the intercept was then added in quadrature to the uncertainty in the electrophoretic mobility (recorded at position E) in order to give a measure of overall uncertainty in the surface zeta potential. A linear fit avoids the region beyond point D whilst, conversely, extending as far out as possible from the surface, in order to provide a more accurate estimate of the slope and thereby the intercept.

Figure 12:
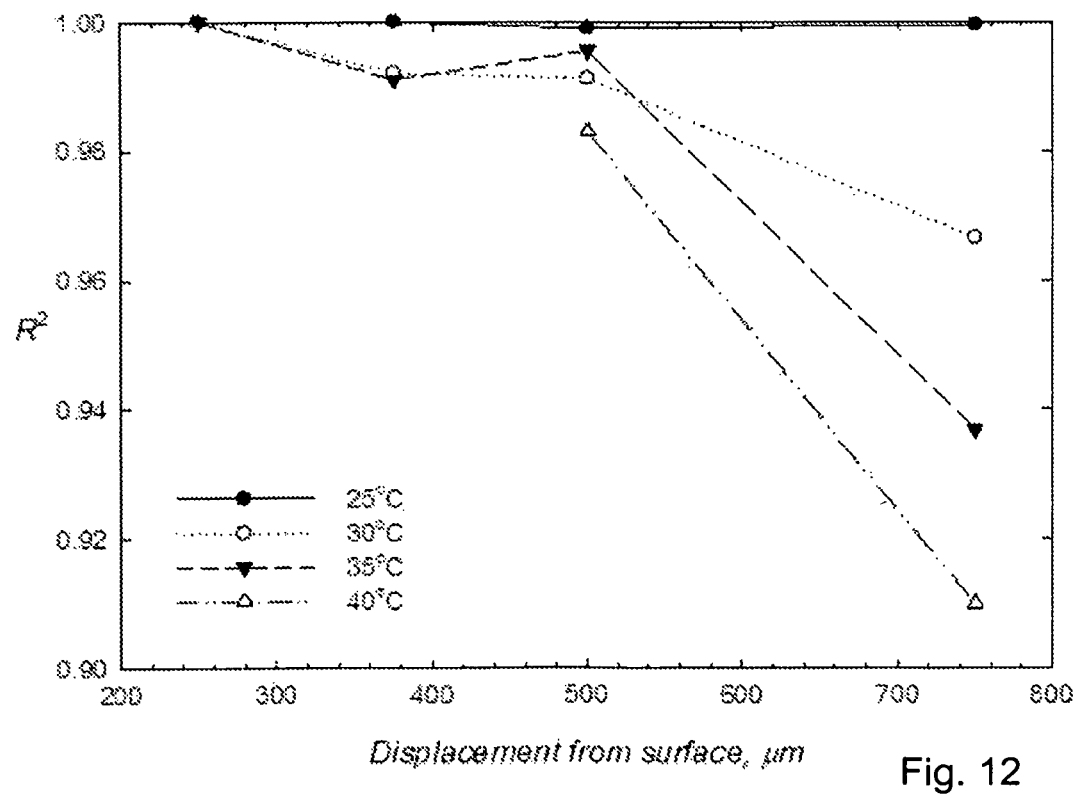
FIG. 12 is a plot of $R^2$ as a function of displacement for water at various temperatures.

The viscosity of the dispersant in which the cell is immersed will change with temperature. Specifically, less viscous fluids will couple less efficiently with increasing distance from the sample surface and therefore we would expect higher temperatures to exhibit a lower electro-osmotic component at the same distance than at lower temperatures. To assess this, a silica plate was measured in 1 mM KCl at pH7.0+/−0.1 using a milk substitute as the tracer. The results are presented in the form of $R^2$ values of the mean values of reported potential at displacements of up to y=750 μm and for a range of temperatures, as plotted in FIG. 12. At 25° C. the fit is good (indicated by an $R^2$ value close to 1) out to greater than 750 μm but, as expected, as the temperature increases the linear region reduces in extent with even a 5° C. increase in temperature enough to reduce the $R^2$ value from >0.99 to approximately 0.97 at 750 μm. As a result, measurements are preferably conducted at or around ambient temperature, nominally 25° C., and with a maximum displacement set by the point at which the $R^2$ value falls below 0.99.

Figure 13:
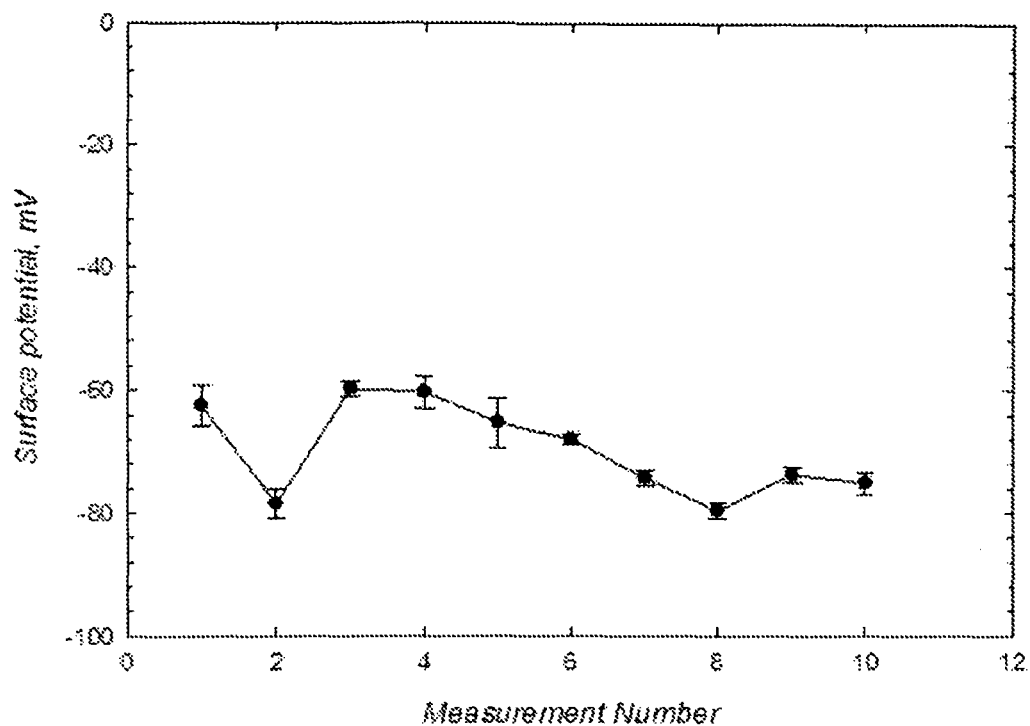
FIG. 13 is a plot of surface potential for a series of measurements for a PTFE sample.

Various measurements were performed to demonstrate the accuracy, precision and reproducibility of the new technique using a comparison with measurements by other techniques reported in the literature. Reproducibility of the technique was investigated for a known well behaved system of a PTFE block and 300 nm carboxylated latex beads dispersed in pH9.2 buffer. Latex is known to have a stable zeta potential of −68 mV+/−10% at this pH, which can be measured using Laser Doppler Electrophoresis (LDE) for extended periods without degradation. Measured surface potentials of the PTFE sample are shown in FIG. 13. Each experiment was conducted with a new tracer dispersion and after having cleaned the PTFE block and electrodes with Helmanex® followed by copious amounts of deionised water and a brush.

TABLE 1

Literature values for PTFE surface potential in a 1 mM salt solution at pH 9.

| | Surface Potential/mV | Reference |
|---|---|---|
| Capillary electrophoresis | −57 | [6] |
| Streaming potential | −78 | [1] |
| Capillary electrophoresis | −65 | [7] |

No outliers were removed from the data in FIG. 13 and the overall surface zeta potential result of −70.0 mV+/−7.5 mV is in excellent agreement with the mean value from the available literature values indicated in Table 1 above of −67.0 mV+/−11 mV. The Goethite, NIST traceable standard for dispersed zeta potential measurements quotes a pass/fail RSD of 10%, indicating that the technique is capable of reproducing surface potential measurements to approximately the same uncertainty, given by—(7.5/70)× 100%=11%.

Titrations of surface potential against pH are likely to be one of the primary applications for this technique. A series of measurements of PTFE and silica were conducted in 1 mM KCl and the pH varied using HCl and KOH. A milk substitute (described in further detail in reference [35]) was used as a tracer for all measurements. Each pH point corresponds to a separate measurement sequence using the cell.

Figure 14:
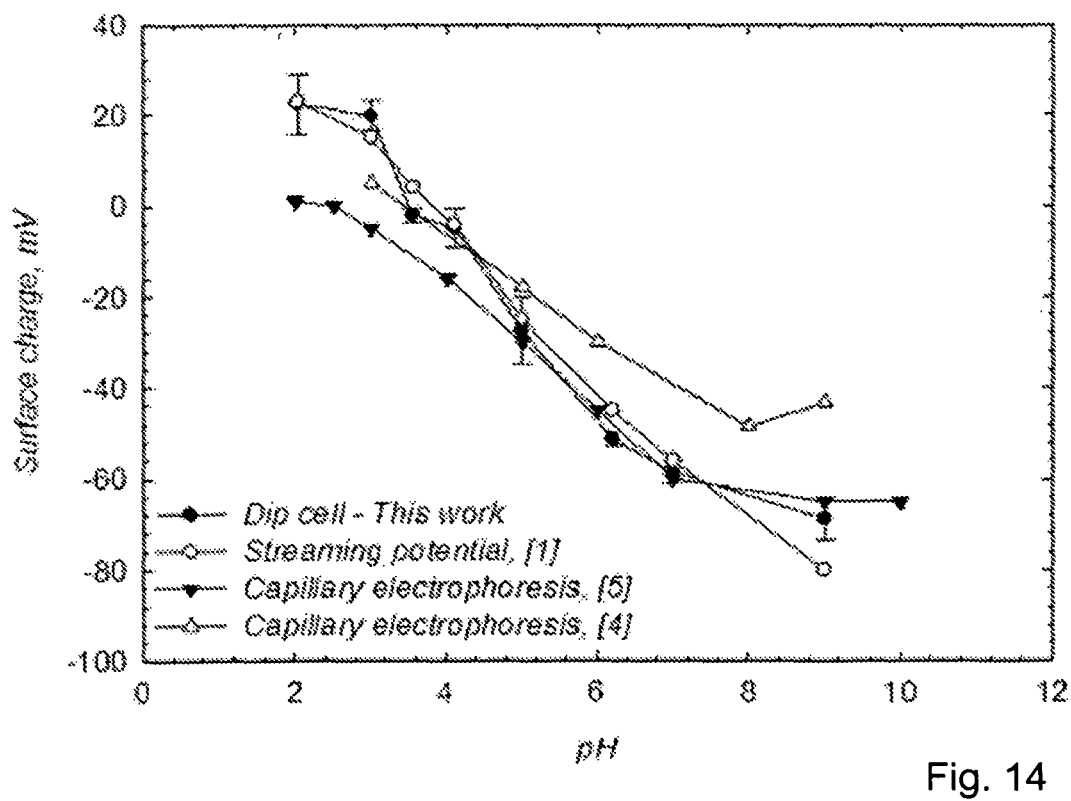
FIG. 14 is a plot of surface charge as a function of pH for a PTFE sample measured using the instrument of FIG. 1 and with other techniques.
Figure 15:
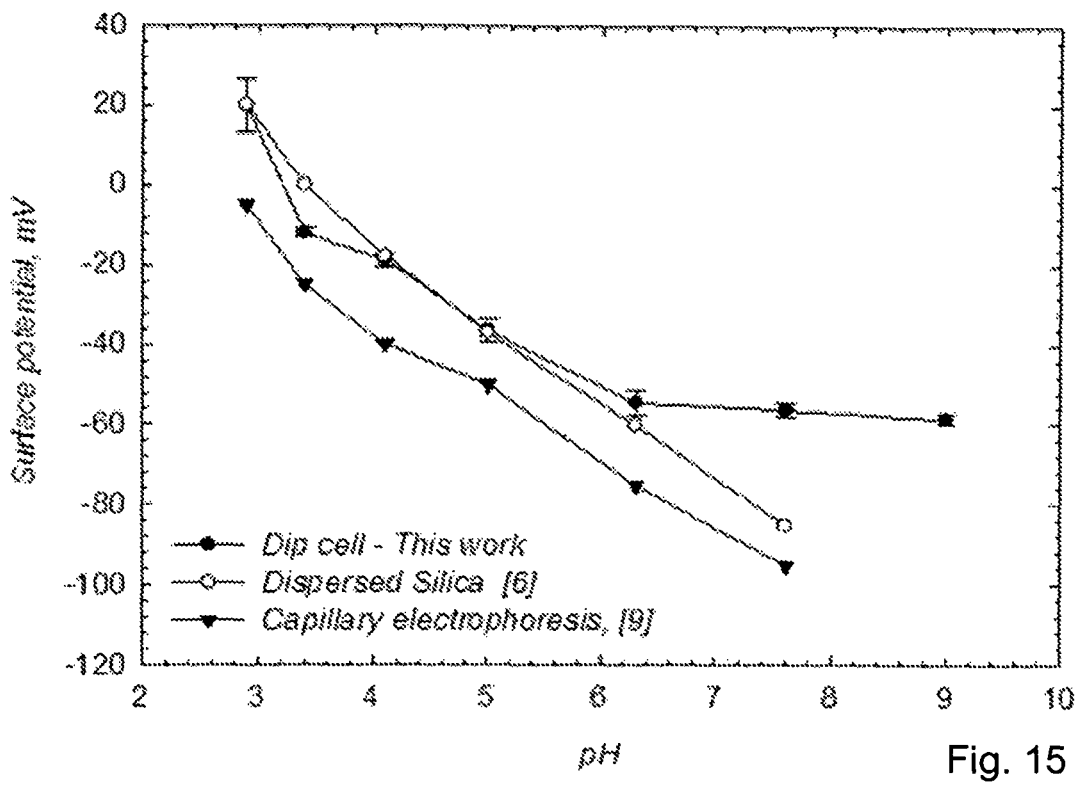
FIG. 15 is a plot of surface potential as a function of pH for a sample of silica measured using the instrument of FIG. 1 and with other techniques.

FIGS. 14 and 15 show that the results are in good general agreement with streaming potential, dispersed particles and capillary electro-osmosis measurements at all pH values tested in the region of the isoelectric point (IEP). There is less general agreement at higher pH values but this appears to be a general feature of all techniques. For data obtained by the new technique, the surface potential would be expected to saturate at high (and low) pH as all available surface charge groups are ionised. Looking at the error bars in both plots, no trend between the uncertainty and pH is seen to exist, with a typical uncertainty of +/−2 to 3 mV. The isoelectric point for the milk substitute is at pH4. No increase in uncertainty in the reported surface potential is detected either when the surface IEP is at approximately the same value as the surface (FIG. 14) or at a different value (FIG. 15). This indicates that the IEP of the tracer may be ignored as long as the experiment does not extend for long enough for it to stick to the surface under test. In this case, each displacement took 120 s to record, but a single dispersion was used for each pH point over five or six displacement positions so the samples were immersed for up to 20 minutes without any apparent reduction in accuracy.

Figure 16:
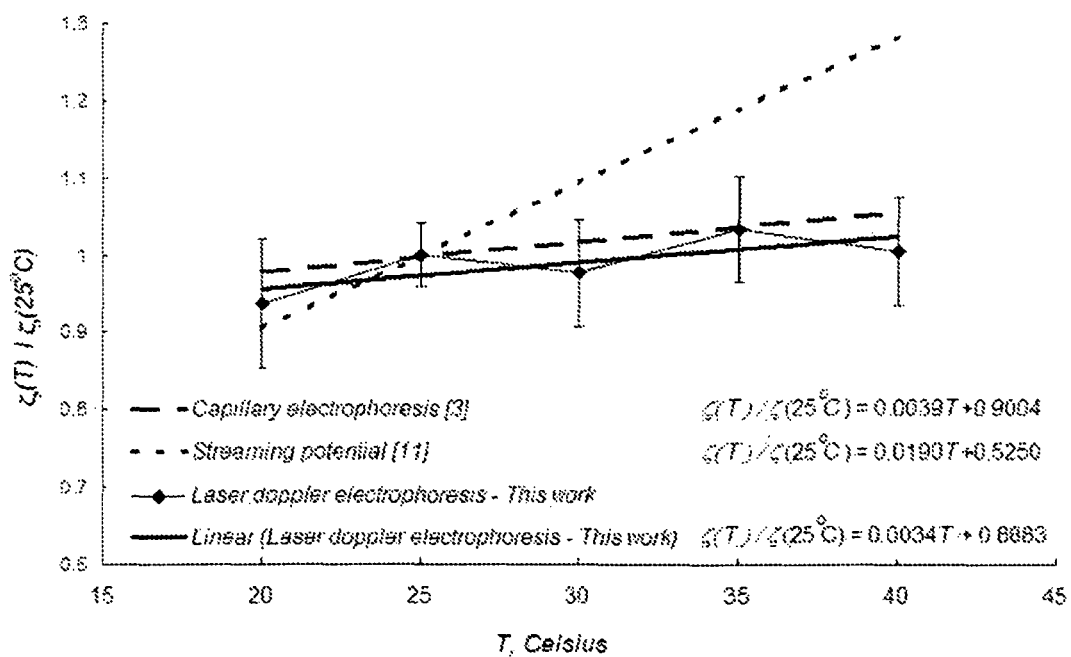
FIG. 16 is a plot of surface potential normalized to a value recorded at 25° C. as a function of temperature for the instrument of FIG. 1 and with other techniques.

Kirby & Hasselbrink (reference [22]) note that the scientific record is sparsely populated with studies concerned with the relationship between surface potential and temperature. A small number of notable contributions exist which strongly disagree with each other. As a comparison, the surface potential of a Silica test plate was measured as an application specific demonstration of the performance of the technique with temperature. Much of the experimental evidence for the relationship between zeta potential and temperature is due to Ishido & Mizutani (reference [2]) and Somasundaran & Kulkani (reference [26]), whose streaming potential measurements predict an increase of 1.75% per ° C. in zeta potential of silica in 1 mM and 10 mM $KNO_3$ at pH7.0. An uncoated microscope slide was cut and mounted in the cell and the surface zeta potential measured in 1 mM KCl at pH 7.0+/−0.1. The data are shown in FIG. 16 with a plot of surface potential, normalized to the value recorded at 25° C., against temperature. Our data predict a slope of 0.34%, which is in poor agreement with the streaming potential results but is in excellent agreement with a more recent study using capillary electrophoresis by Evenhuis et al (reference [5]), who measured a slope of 0.39% per ° C. The error bars demonstrate that the technique is reproducible with temperature variation with an RSD varying from 5% to 10% and that no apparent increase in uncertainty exists with temperature. The whole cell (dip cell, cuvette and dispersant) is immersed in the instrument's temperature controlled cell block and setting each temperature is therefore simpler to implement in comparison to other techniques as the whole apparatus can be kept at the same set temperature (See reference [22]).

Increasing salt concentration increases the current passed for the same field strength, which can cause Joule heating and polarization concentration effects. These can increase the uncertainty in the recorded particle mobility. Surface potential measurements of Polycarbonate and PTFE test blocks in KCl were carried out between 0.1 mM and 50 mM salt concentration with a milk substitute used as the tracer. In order to avoid Joule heating the conductivity of the sample was measured before and after the electrophoresis measurement and the field strength titrated down until the difference in conductivity and therefore sample temperature was negligible. Table 2 below shows the field strengths and subsequent integration times used to maximize the signal to noise at each concentration C, where, pC=−logC.

TABLE 2

Field strength and integration times against pC.

| pC | Field Strength, V/cm | Integration time per displacement point, s |
|---|---|---|
| 1.5 | 6.25 | 25 |
| 2 | 12.5 | 20 |
| 3 | 25 | 13 |
| 4 | 25 | 13 |

Figure 17:
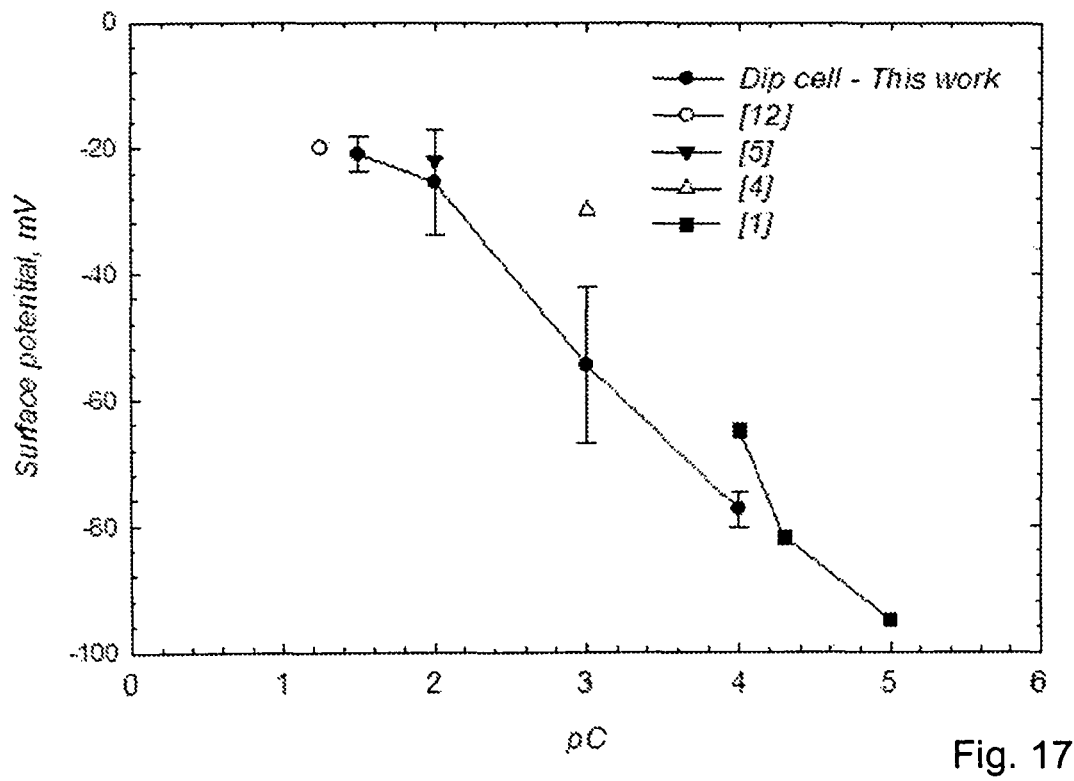
FIG. 17 is a plot of surface potential as a function of pC for a PTFE sample measured using the instrument of FIG. 1 and using other techniques.
Figure 18:
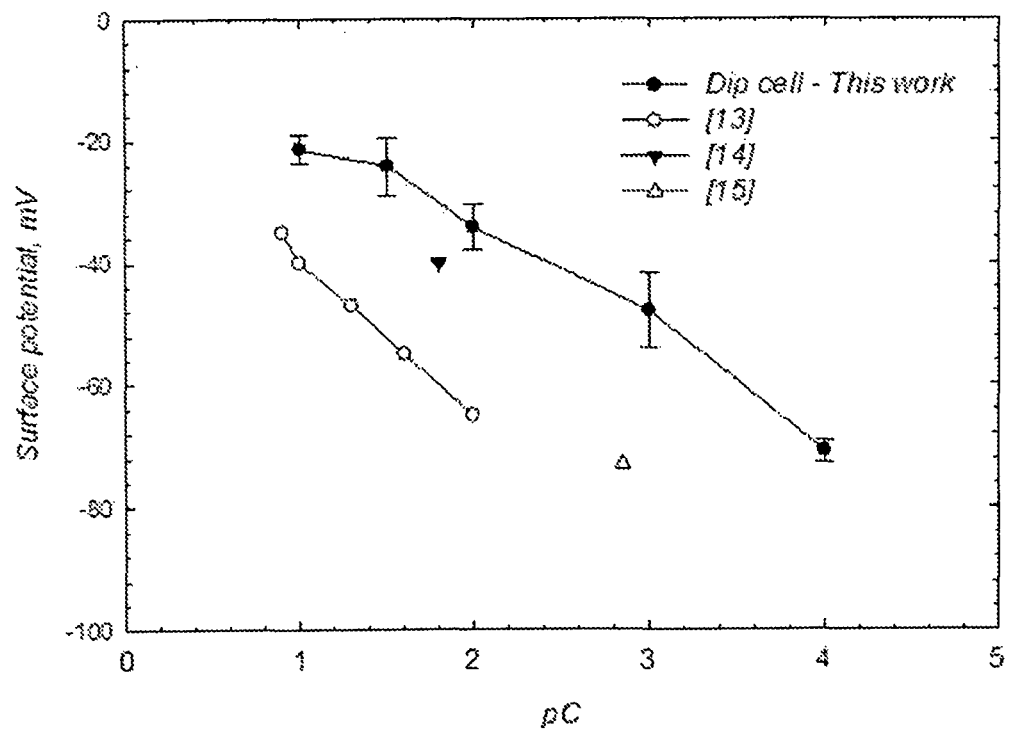
FIG. 18 is a plot of surface potential as a function of pC for a polycarbonate sample measured using the instrument of FIG. 1 and using other techniques.

The data for PTFE are shown in FIG. 17 and for polycarbonate in FIG. 18. Firstly, we note that with the field strengths and integration times used in Table 2, no relationship between the uncertainty in the measurements and pC is apparent. The uncertainties in the PTFE data are of the order of the spread in the mean results from all techniques and significantly less so for the polycarbonate case.

We would expect a linear relationship between surface potential and pC passing through the origin between surface potential and salt concentration for monovalent counter ions. The polycarbonate dip cell data are self consistent in that they fit linearly with near zero intercept but there is considerable variation amongst the references. Since both the dip cell and the Roberts et al data (reference [23]) are linear with low intercept then we can attribute the difference to a genuine difference in sample properties such as surface smoothness, for instance—in our case, the polycarbonate was a small block removed from a moulded part with a highly polished surface. The PTFE results are in good overall agreement with the literature values although an overall intercept of zero is less convincing in these data, with a more likely intercept nearer to +20 mV.

Figure 19A:
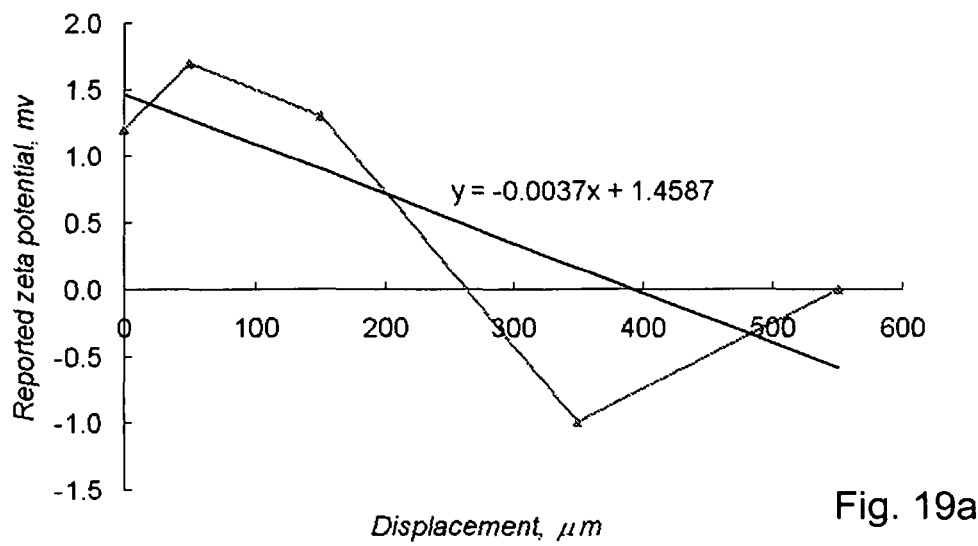
FIG. 19a is a plot of apparent zeta potential as a function of displacement for a sample of clean PTFE in Goethite at pH 3.5.
Figure 19B:
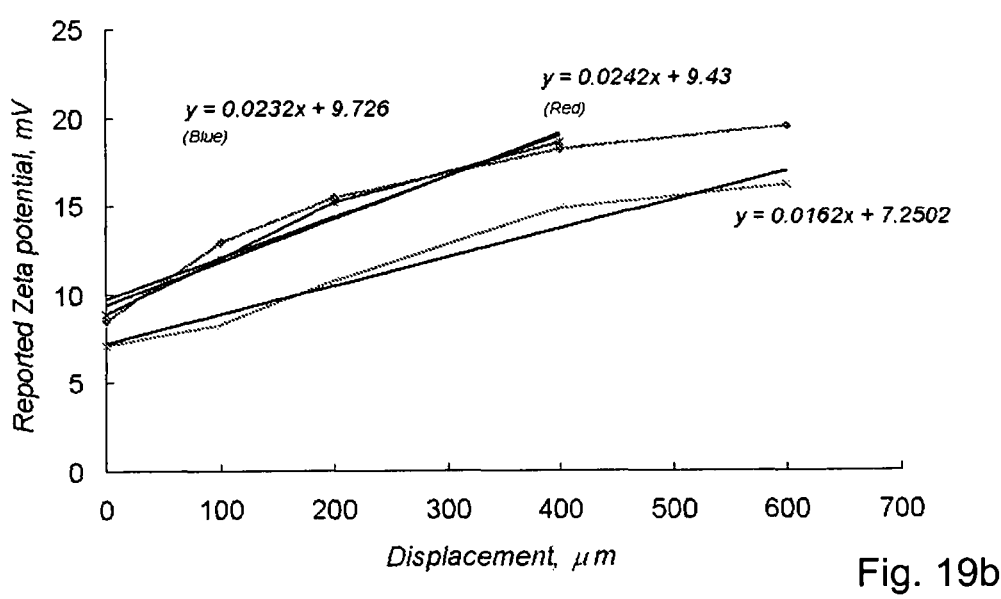
FIG. 19b is a plot of apparent zeta potential as a function of displacement for a sample of PTFE with dried-on Goethite in Goethite at pH 3.5.
Figure 19C:
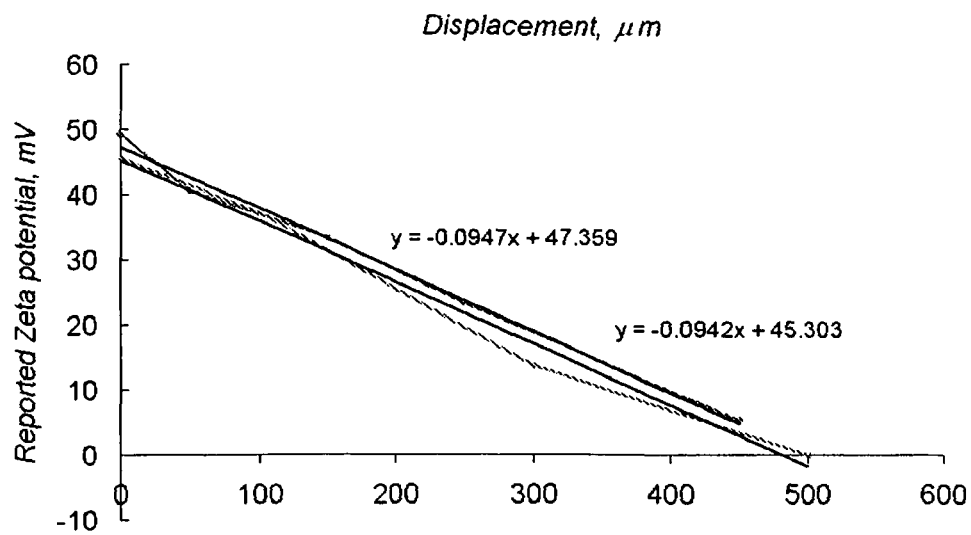
FIG. 19c is a plot of apparent zeta potential as a function of displacement for a sample of PEEK 450G in DTS0230 at pH 9.0.
Figure 19D:
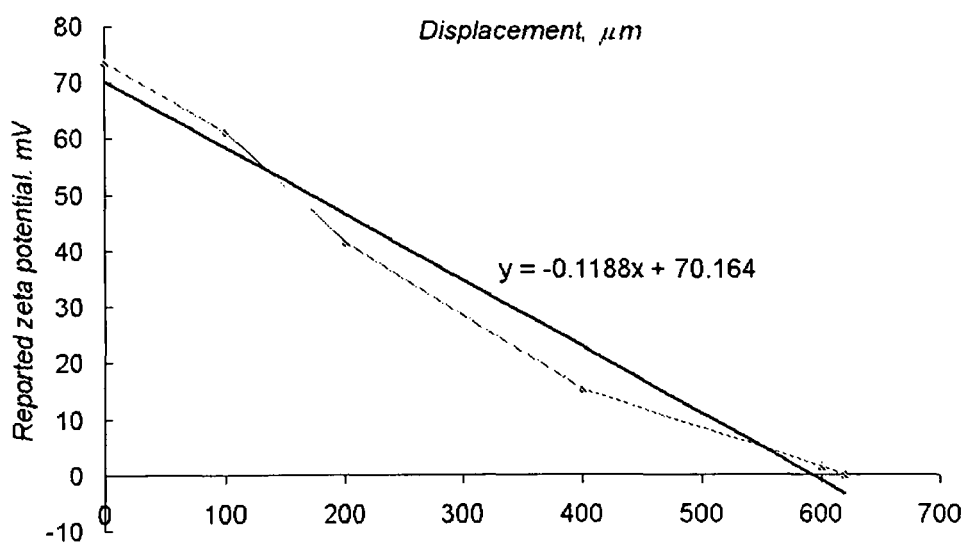
FIG. 19d is a plot of apparent zeta potential as a function of displacement for a sample of PTFE in DTS0230 at pH 9.0.
Figure 20A:
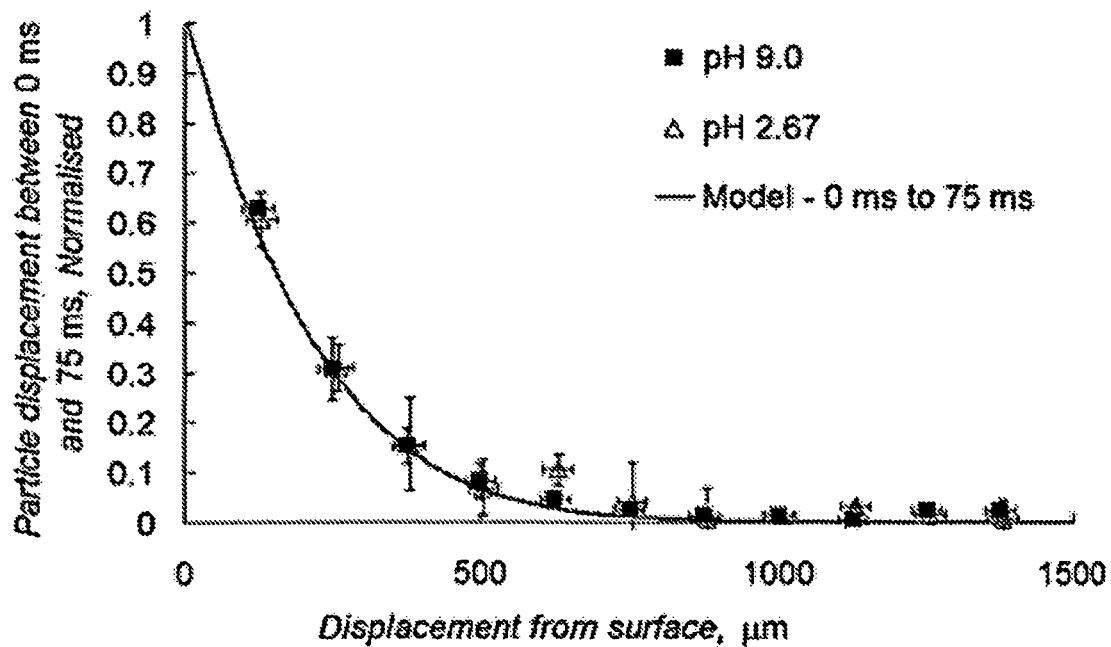
FIGS. 20a to 20e are plots of normalised particle displacement measurements over time intervals varying between 75 ms (FIG. 20a) and 600 ms (FIG. 20e) as a function of displacement from the surface of a smooth flat PTFE block in 1 mM KCl at pH 9.0 and pH 2.67.
Figure 20B:
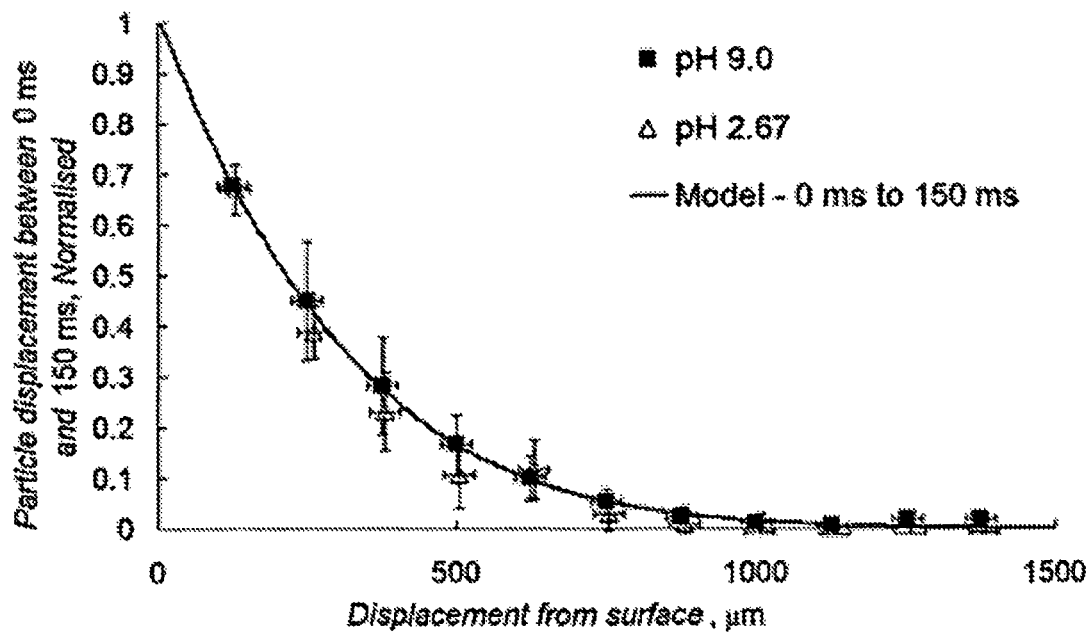
Figure 20C:
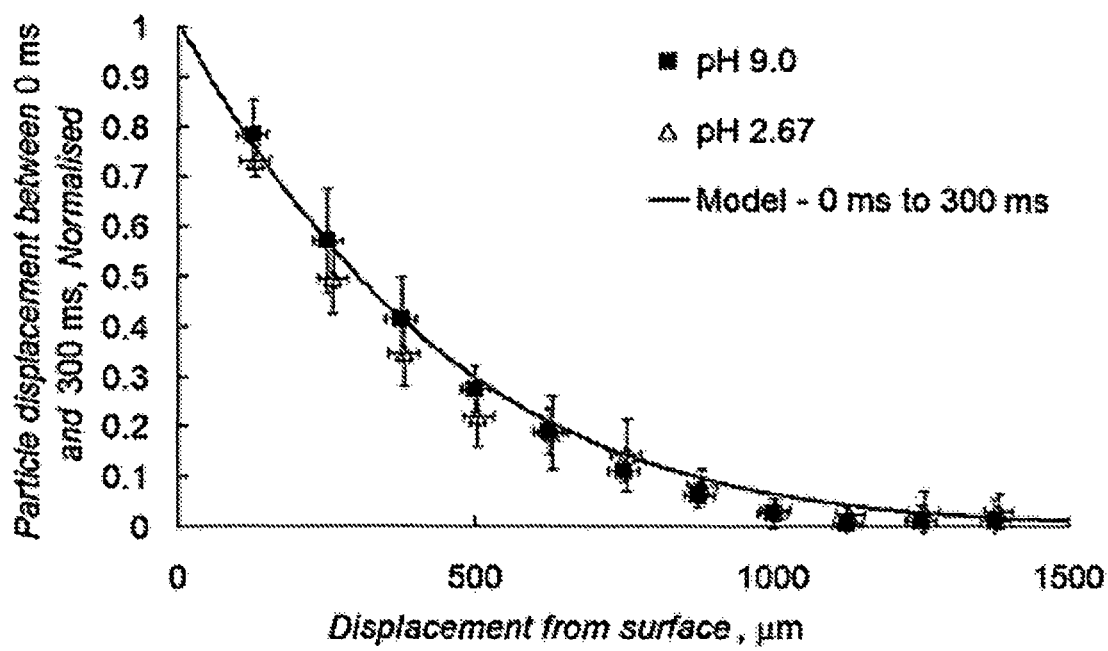
Figure 20D:
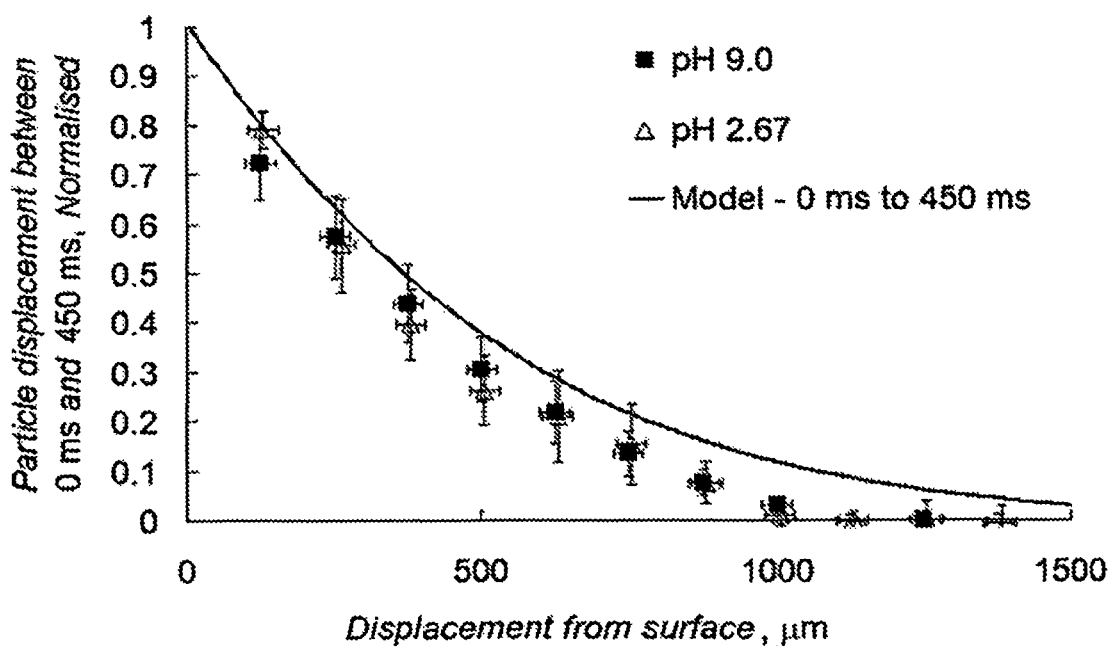
Figure 20E:
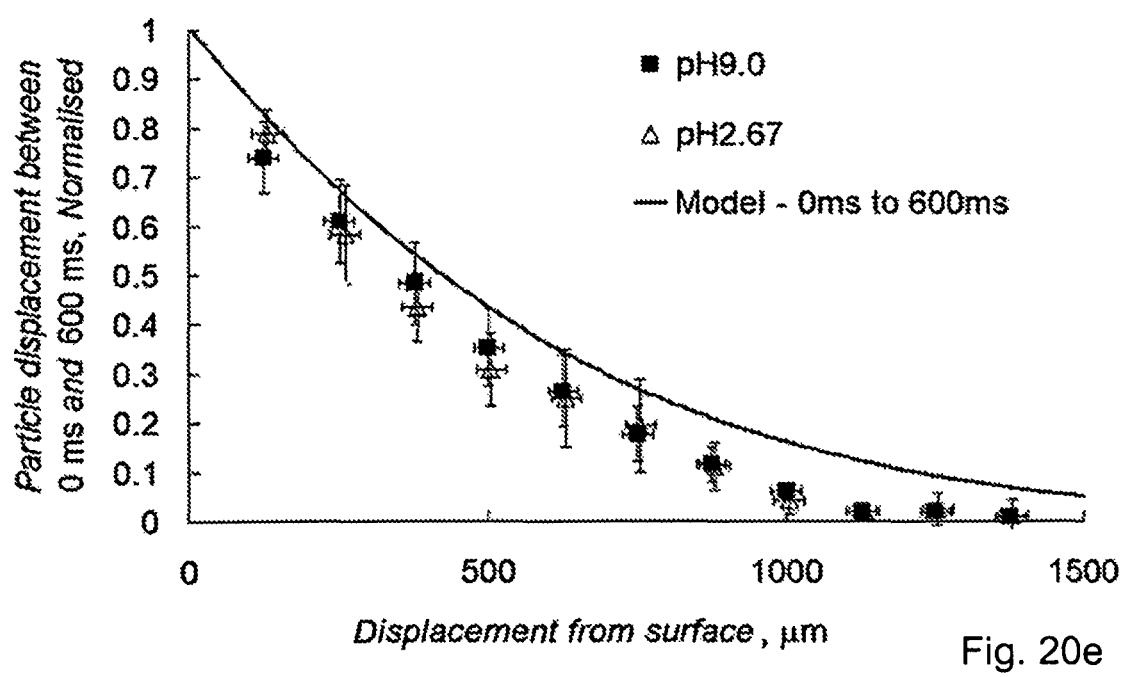

FIGS. 19a to 19d illustrate further results of reported zeta potential for various combinations of samples and electrolytes. FIG. 19a indicates results from a clean PTFE plate in a Goethite solution at pH 3.5. FIG. 19b indicates results from a PTFE plate having dried-on Goethite in a Goethite solution at pH 3.5. The differences between these sets of measurements indicate the importance of ensuring a clean sample to obtain accurate measurements of the sample material uncontaminated by suspended or dissolved material in the electrolyte. FIG. 19c indicates results from a PEEK 450G plate in a DTS023 solution at pH 9.0, and FIG. 19d indicates results from a PTFE plate in the same type of solution. The results from these measurements are summarised below in Table 3, with selected results compared with those from reference [1].

TABLE 3

Summary of results from FIGS. 19a-d, in comparison with literature values (*streaming potentials from reference [1]).

| Test surface | Tracker particle | pH | Measured wall charge | Streaming potential result* |
|---|---|---|---|---|
| PTFE | Carboxylated latex | 9.0 | −70 mV | −80 mV pH 9.0 KCl |
| PEEK 450G | Carboxylated latex | 9.0 | −45 mV | |
| PTFE with dried on Goethite | Goethite | 3.5 | 10 mV | |
| PTFE | Goethite | 3.5 | −1.5 mV | 2.5 mV pH 3.5 KCl |

FIGS. 20a to 20e illustrate plots of normalised particle displacement measurements for time intervals between 0 and 75 ms (FIG. 20a), 0 and 150 ms (FIG. 20b), 0 and 300 ms (FIG. 20c), 0 and 450 ms (FIG. 20d) and 0 and 600 ms (FIG. 20e) for a smooth, flat PTFE block mounted and measured in 1 mM KCl at pH 9.0 and pH 2.67. At pH 9.0 the surface is highly negatively charged and at pH 2.67, highly positively charged (see reference [1]). The milk substitute used for the tracer particles was also negative at pH 9.0 and positive at pH 2.67 (see further details in Appendix B of reference [35]). Each field half cycle was 600 ms in total duration. A least square linear fit was applied to the phase plot (FIG. 10a) over various subsets of 75 ms, 150 ms, 300 ms, 450 ms and 600 ms of this interval to yield an average phase shift per unit time at each displacement point A-E. The total particle displacement in the time interval in question, at each distance from the test surface, is directly proportional to the average total phase shift during the ontime pulse (FIG. 8a). This total particle displacement is plotted in each of FIGS. 20a to 20e. The experimental data were also normalised between a 2nd order polynomial extrapolation of the data to the intercept (y=0) and from an estimate of the asymptote towards point E indicated in FIG. 9. This asymptote is due to the limiting electrophoretic mobility of the tracer particles in the absence of any electro-osmotic flow far from the surface. Normalisation removes the tracer velocity and allows direct comparison of the data with the model indicated by equation (4) above. The fit to the model is excellent for the phase data at and below 300 ms for both positively and negatively charged surfaces. Above 300 ms the fit is less convincing and we attribute this to a gradual build up in back pressure which works to suppress the electro-osmotic flow. Further explanation of these results, and the associated model, is disclosed in reference [35], the contents of which are incorporated by reference herein.

In conclusion, a new, simpler technique for the measurement of surface zeta potential using laser Doppler electrophoresis has been presented. The technique is shown to be characterized by a relative standard deviation in reproducibility of less than or equal to around 10% for well behaved systems, yielding accurate and reproducible surface potential values in excellent agreement with literature values from streaming potential, electro-osmotic (capillary) flow and particle dispersions for various surface types, temperatures up to 40° C. and ionic strengths in the range 0.1 mM to 50 mM.

In the embodiment described, control and measurement functions can be performed by a computer workstation running a standard operating system, such as Microsoft Windows ®or Linux ®, and special-purpose software. The workstation can allow the user to perform individual measurements, and it can also use sequencing functionality to fully automate electrical and mechanical operations. It is also possible to create an implementation that is based on specialized custom hardware, or a combination of the two approaches.

The present invention has now been described in connection with a number of specific embodiments thereof. However, numerous modifications which are contemplated as falling within the scope of the present invention should now be apparent to those skilled in the art. For example, while micrometer- and joggle-based approaches have been shown to adjust the detection position, other approaches such as moving mirrors could also be employed. Therefore, it is intended that the scope of the present invention be limited only by the scope of the claims appended hereto. In addition, the order of presentation of the claims should not be construed to limit the scope of any particular term in the claims. All documents referenced in this application are herein incorporated by reference for all purposes.

REFERENCES

[1.] C. Werner, H. Körber, R. Zimmerman, S. Dukhin, H.-J. Jacobasch, "Extended electrokinetic characterisation of flat solid surfaces", J. Colloid Interface Sci. 208 (1998) 329-346.

[2] T. Ishido, H. J. Mizutanio, J. Geophys. Res. 86 (1981) 1763-1775.

[3] I. Gusev, C. J. Horváth, J. Chromatogr. A 948 (2002) 203-223.

[4] J. Hoggard, P. Sides, D. Prieve, Langmuir 21 (16) (2005) 7433-7438.

[5] C. J. Evenhuis, R. M. Guijt, M. Macka, P. J. Marriot, P. R. Haddad, Electrophoresis 27 (2006) 672-676.

[6] J. C. Reijenga, G. V. A. Aben, T. P. M. Verheggen, F. M. Everaerts, J. Chromatogr. A 260 (1983) 241-254.

[7] W. Schutzner, E. Kenndler, Anal. Chem. 64 (1992) 1991-1995.

[8] M. Kosmulski, E. Matijevic, Langmuir 8 (1992) 1060-1064.

[9] A. Doren, J. Lemaitre, P. G. Rouxhet, J. Colloid Interface Sci. 130 (1989) 1.

[10] S. Nakamura, Membrane 30 (6) (2005) 344-347.

[11] R. J. Hunter, Zeta Potential in Colloid Science, Academic Press, 1981.

[12] K. Schatzel, J. Merz, "Measurement of small electrophoretic mobilites by light scattering and analysis of the amplitude weighted phase structure function", J. Q3 Chem. Phys. 81 (5).

[13] B. J. Berne, R. Pecora, Dynamic Light Scattering, Dover, 2000.

[14] K. Schatzel, W. Wiese, A. Sobotta, M. Drewel, "Electroosmosis in an oscillating field: avoiding distortions in measured electrophoretic mobilities", J. Colloid Interface Sci. 143 (1991) 287-293.

[15] M. Minor, A. J. van der Linde, H. P. van Leeuwen, J. Lyklema, "Dynamic aspects of electrophoresis and electroosmosis: a new fast method for measuring particle mobilities", J. Colloid Interface Sci. 189 (1997) 370-375.

[16] P. J. Scales, F. Grieser, T. W. Healy, Langmuir 8 (1992) 965-974.

[17] J. Y. Chen, C.-H. Ko, S. Bhattacharjee, M. Elimelech, Colloids Surf. A: Phys. Eng. Aspects 191 (2001) 3.

[18] P. J. Sides, J. Newman, J. D. Hoggard, D. Prieve, Langmuir 22 (2006) 9765.

[19] P. J. Sides, D. Faruqui, A. J. Gellman, Langmuir 25 (2009) 1475-1481.

[20] S. Nishimura, P. J. Scales, H. Tateyama, K. Tsunematsu, T. W. Healy, Langmuir 11 (1995) 291.

[21] K. D. Lukacs, J. W. Jorgensen, J. High Resolut. Chromatogr. 8 (1985) 407-411.

[22] B. Kirby, E. F. Hasselbrink Jr., Electrophoresis 25 (2004) 187-202.

[23] M. A. Roberts, J. S.-Rossier, P. Bercier, H. Girault, Anal. Chem. 69 (1997) 2035-2042.

[24] B. Kirby, E. F. Hasselbrink Jr., Electrophoresis 25 (2004) 203-213.

[25] S. A. Soper, A. C. Henry, B. Vaidya, M. Galloway, M. Wabuyele, R. L. McCarley, Anal. Chim. Acta 470 (2002) 87-99.

[26] Somasundaran P, Kulkani R D, J. Colloid Interface Sci., 45, (1973), 591-600.

[27] U.S. Pat. No. 7,217,350

[28] U.S. Pat. No. 7,449,097

[29] US 2011/0210002

[30] EP 2423671

[31] WO/2010/041082

[32] U.S. Pat. No. 7,217,350

[33] U.S. Pat. No. 7,295,311

[34] EP 0990888

[35] J. C. W. Corbett et al, "Measuring surface zeta potential using phase analysis light scattering in a simple dip cell arrangement", Colloids and Surfaces A: Physicochemical and Engineering Aspects, Volume 396, 20 Feb. 2012, Pages 169-176.

The invention claimed is:

1. A zeta potential measurement accessory, comprising:
a static section including a first support surface for supporting the static section with respect to an upward-facing cuvette,
a sample support surface for holding a sample, which sample support surface is positioned inside the cuvette facing downward when the static section is supported with respect to the upward-facing cuvette by the first support surface,
a pair of electrodes facing each other below the sample support surface when the static section is supported with respect to the upward-facing cuvette by the first support surface, wherein the sample support surface is located between the electrodes, and
an adjustment mechanism operatively connected between the static section and the sample support surface and operative to move the sample support surface vertically with respect to the static section when the static section is supported with respect to the upward-facing cuvette by the first support surface.

2. The accessory of claim 1 wherein the static section includes a second support surface for supporting the static section at a different height from the height at which the static section is supported by the first support surface.

3. The accessory of claim 1 wherein the adjustment mechanism is motorized.

4. The accessory of claim 1 wherein the adjustment mechanism is manual.

5. The accessory of claim 4 wherein the adjustment mechanism includes a micrometer.

6. The accessory of claim 1 wherein the first support surface is constructed to be supported by an upper surface of the cuvette.

7. The accessory of claim 1 further including an adjustment jig including a contact surface for contacting at least the first support surface of the static section and a contact surface for contacting a sample on the sample support surface.

8. The accessory of claim 1 further including tracer particles for performing measurements with the accessory.

9. The accessory of claim 1 further including an electrical interface for connection to a zeta potential measuring instrument.

* * * * *